United States Patent
Lax

(10) Patent No.: US 6,776,617 B2
(45) Date of Patent: Aug. 17, 2004

(54) DENTAL POST WITH COUNTERSINK

(76) Inventor: Steven Lax, 264 E. Broadway, Apt C201, New York, NY (US) 10002

( * ) Notice: Subject to any disclaimer, the term of this patent is extended or adjusted under 35 U.S.C. 154(b) by 107 days.

(21) Appl. No.: 10/151,765

(22) Filed: May 21, 2002

(65) Prior Publication Data

US 2003/0219700 A1 Nov. 27, 2003

(51) Int. Cl.⁷ .................................................. A61C 5/08
(52) U.S. Cl. ...................................................... 433/221
(58) Field of Search ................................ 443/221, 220, 443/165, 224, 225, 223

(56) References Cited

U.S. PATENT DOCUMENTS

| | | | |
|---|---|---|---|
| 347,975 A | 8/1886 | Starr | |
| 403,428 A | 5/1889 | Hansen | |
| 616,302 A | 12/1898 | Evans | |
| 984,782 A | 2/1911 | Starr | |
| 1,109,080 A | 9/1914 | Merker | |
| 1,228,488 A | * 6/1917 | Shaw | 433/221 |
| 1,479,508 A | 1/1924 | Maeulen et al. | |
| 1,589,994 A | 6/1926 | Simmons | |
| 3,508,334 A | 4/1970 | Weissman | |
| 4,427,383 A | 1/1984 | Goldman | |
| 4,446,579 A | 5/1984 | Inamori et al. | |
| 4,449,937 A | 5/1984 | Weissman | |
| 4,543,065 A | 9/1985 | Bushway | |
| 4,588,381 A | 5/1986 | Caracciolo | |
| 4,600,391 A | 7/1986 | Jacob | |
| 4,708,655 A | * 11/1987 | Weissman | 433/225 |
| 4,759,714 A | 7/1988 | Svegvary | |
| 4,778,388 A | 10/1988 | Yuda et al. | |
| 4,820,159 A | * 4/1989 | Weissman | 433/225 |
| 4,828,496 A | * 5/1989 | Lococo | 433/224 |
| 4,846,685 A | 7/1989 | Martin | |
| 4,850,870 A | 7/1989 | Lazzara et al. | |
| 5,066,230 A | * 11/1991 | Weissman | 433/165 |
| 5,326,263 A | 7/1994 | Weissman | |
| 5,348,476 A | 9/1994 | Cohen et al. | |
| 5,487,664 A | 1/1996 | Weissman | |
| 5,775,910 A | 7/1998 | Orrico | |
| 5,919,044 A | 7/1999 | Sicurelli et al. | |
| 6,135,775 A | 10/2000 | Weissman | |
| 6,183,255 B1 | 2/2001 | Oshida | |

* cited by examiner

Primary Examiner—Todd E. Manahan
(74) Attorney, Agent, or Firm—Notaro & Michalos P.C.

(57) ABSTRACT

A dental post and method for supporting a tooth replacement on a natural tooth root, has a shank with a first root engagement portion and a second tooth replacement support portion. A non-round flange is on the first portion but is adjacent the second portion. The non-round flange is received in a non-round countersink at the opening of the root canal for precluding relative rotation between the post and the root. One or more flexible flanges extend from one or both of the shank portions and the entire post is made of plastic.

23 Claims, 4 Drawing Sheets

FIG. 10
FIG. 11
FIG. 12
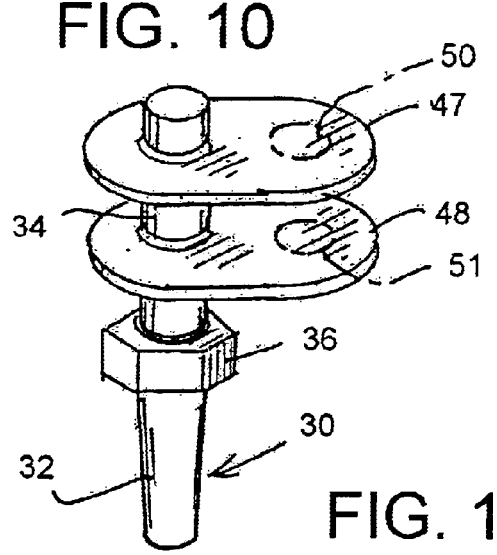
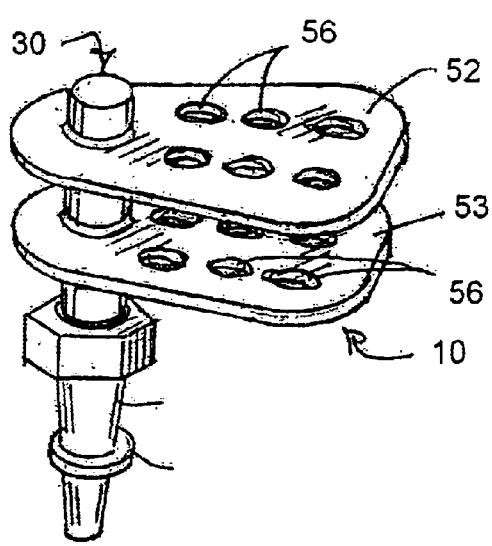
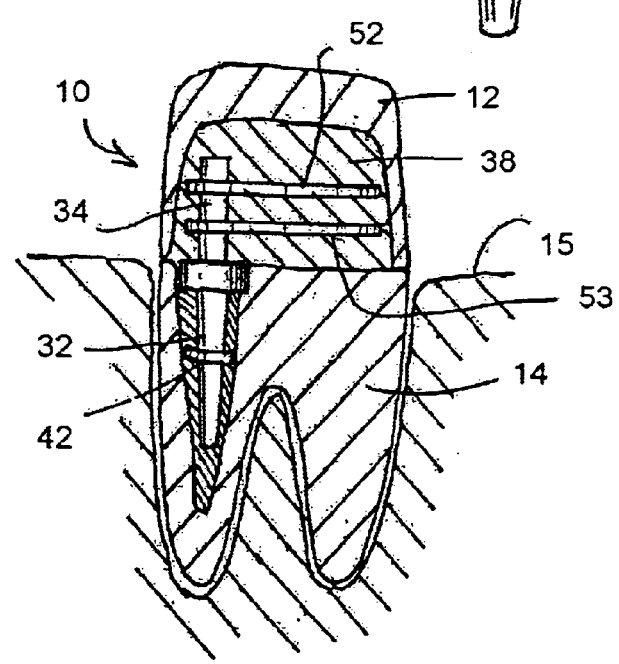

DENTAL POST WITH COUNTERSINK

FIELD AND BACKGROUND OF THE INVENTION

The present invention relates generally to the field of dentistry and, in particular, to and new and useful dental post for supporting a tooth replacement on a natural tooth root, the tooth root having a hollow canal from which a nerve has been removed, the canal having an outer opening and the root having a non-round counter-sink at the top of the tooth root which communicate with the canal opening.

A wide variety of posts are known for use in supporting tooth replacements such as crowns, bridges or other structures above a patients gum line. The posts are usually made of strong metal and have shanks that extend in, and are cemented to hollow root canals prepared by the dentist by drilling out the dead root and other tissue from a damaged tooth.

Although usually made entirely rigid, a flexible post is disclosed by U.S. Pat. No. 5,919,044 to Sicurelli, Jr. et al. This flexible post is made from fiberglass or optical fibers suitable for medical use. U.S. Pat. No. 6,135,775 to Weisman also discloses a post made of plastic.

A dental post with a tapered, polygonal cross-section is disclosed in U.S. Pat. No. 347,975 to Starr. U.S. Pat. No. 403,428 to Hansen discloses an artificial tooth plug having a conical shank with threads for inserting into a tooth root and a larger diameter collar around the base. The collar provides protection over the root but does not extend into the root.

U.S. Pat. No. 616,302 to Evans discloses a post and disk for attaching crowns. The post is secured inside the root socket and the disk, which has a larger diameter than the post, prevents downward movement and supports an artificial tooth externally. U.S. Pat. No. 984,782 to Starr teaches a crown pin having a generally cylindrical lower portion with a flattened side and a perpendicular plate at one end that also extends over a tooth root. Also see U.S. Pat. Nos. 1,109,080 and 1,479,508, for other dental post structures.

A dental post having a polygonal perimeter for the crown but not for the tooth root, is disclosed in U.S. Pat. No. 1,589,994 to Simmons. U.S. Pat. No. 3,508,334 to Weissman disclosed a guide post with flange and drill guides but is not meant to be a permanent part of the patients dental work. U.S. Pat. No. 4,427,383 to Goldman teaches a tooth reconstruction having a threaded screw and a hex nut which is inside and supports an artificial tooth. U.S. Pat. No. 4,449,937 to Weissman shows a dental anchor having a threaded implant portion, a flange and a square anchoring portion secured to the opposite side of the flange. The flange is intended to prevent further movement into a tooth root canal, while the anchoring portion prevents rotation of a dental prosthesis connected using the anchor. These parts of the post are in the crown and not the tooth root.

Also see U.S. Pat. Nos. 4,543,065 and 4,588,381. U.S. Pat. No. 4,600,391 to Jacob teaches a cylindrical countersink flange for being seated in a cylindrical countersink at the top of a tooth root canal. This structure does not and cannot not resist rotation of the post in the root since rotation is, in fact, necessary to install this threaded post. A cylindrical, and therefore rotatable, countersink is also taught by U.S. Pat. No. 5,348,476 to Cohen et al.

See U.S. Pat. No. 4,759,714 to Szegvary which discloses a post with threaded shank post that is fixed into the root with the ususal composite cement, and an upper crown supporting portion with rigid side ribs for extending into the luting cement inside a crown. Other posts with threads of other structures to help secure the post shank are disclosed in U.S. Pat. Nos. 4,778,388; 4,846,685; 5,066,230 and 5,326,263.

A need remains for an improved post which will not rotate in the root and which securely supports a tooth replacement.

SUMMARY OF THE INVENTION

It is an object of the present invention to provide a dental post and method for supporting a tooth replacement on a natural tooth root having a hollow canal from which a nerve has been removed, which provides a non-round countersink at the top of the tooth root, communicating with the canal opening.

Another object of the invention is to provide a post having a shank with a first root engagement portion for extending into the hollow canal, and a second tooth replacement support portion for extending out of the canal. The post has a non-round flange formed as one piece with the shank on the first portion but adjacent the second portion, the non-round flange being adapted to be received in the non-round countersink for precluding relative rotation between the post and the root when the first root engagement portion is in the root.

Another object of the invention is to provide a dental post including at least one flexible flange formed as one piece with the shank and extending outwardly from either the first or the second portions of the shank, or both. According to another object of the invention, two to three flexible flanges extend outwardly from the first root engagement portion in the root and two to three such flanges also extend outwardly from the second, tooth replacement receiving or support portion of the shank.

A still further object of the invention is to manufacture the post entirely of a suitably strong and biocompatible plastic that is capable of being cemented to the root and to which a crown or other tooth replacement can be cemented.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 10 is a perspective view of another embodiment of the post of the invention;

FIG. 11 is a perspective view of another embodiment of the dental post of the present invention; and FIG. 12 is a sectional view of a still other embodiment of the post of the invention in a tooth with more than one root.

DESCRIPTION OF THE PREFERRED EMBODIMENTS

Figure 7:
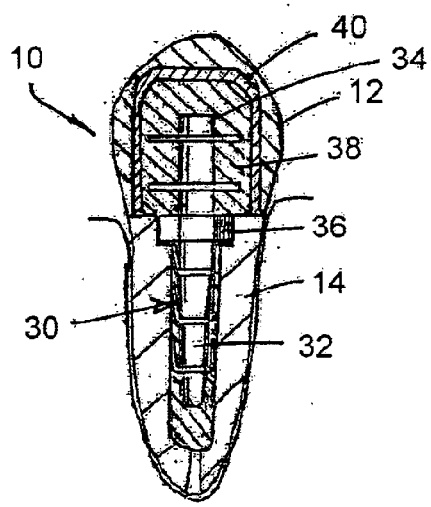
FIG. 7 is a view similar to FIG. 6 of the next step in which the tooth replacement has been cemented to the top of the post preparation.
Figure 8:
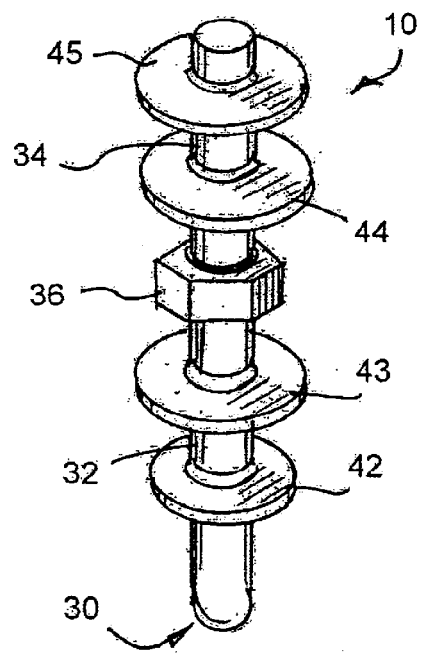
FIG. 8 is a perspective view of another embodiment of the dental post of the present in invention.

Referring now to the drawings, in which like reference numerals are used to refer to the same or functionally similar parts, FIG. 8 illustrates a dental post of the present invention, generally designated 10, for supporting a tooth replacement such as a crown 12 shown in FIG. 7, on natural tooth root 14 also shown in FIG. 7.

Figure 1:
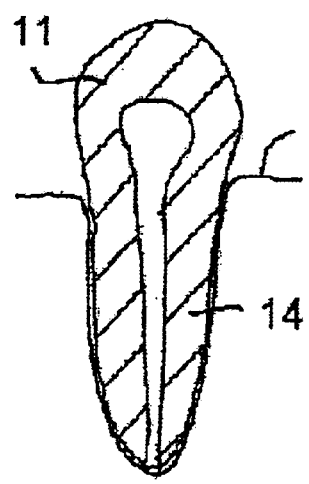
FIG. 1 is a sectional view of a damaged tooth on which a root canal procedure of the present invention is to be performed.
Figure 2:
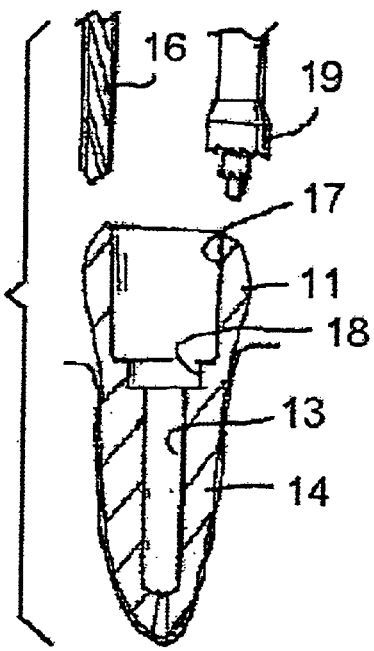
FIG. 2 is a view similar to FIG. 1, of the tooth after the tooth head has been hollowed out, a hollow canal has been drilled into the tooth to remove the nerve and some surrounding tissue, and a cylindrical countersink bore has been made at the top of the canal.

FIGS. 1 to 7 illustrate a method according to the invention. As shown in FIG. 1, a damaged tooth with a natural crown 11 and root 14 in gum or gingival tissue 15, is to be treated.

The method of the invention for mounting a tooth replacement such a crown 12, to the natural tooth root 14, starts with the step of drilling a hollow canal 13 in the tooth root 14, to remove the nerve and surrounding tissue in a usual manner using a dental drill or burr 16. The canal has an outer opening which is enlarged in the natural crown to hollow out the crown at 17, again using a know drill and technique. The next step is drilling a round countersink at the top of the tooth root at 18, which communicates with the canal opening and canal 13. This is done with a know countersink drill 19

Figure 3:
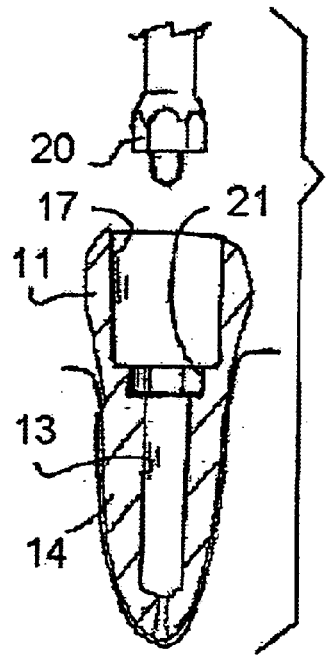
FIG. 3 is a view similar to FIG. 2 of the next step in a method of the invention which uses an ultrasonic cutting head to convert the initially cylindrical countersink into a non-round countersink.
Figure 4:
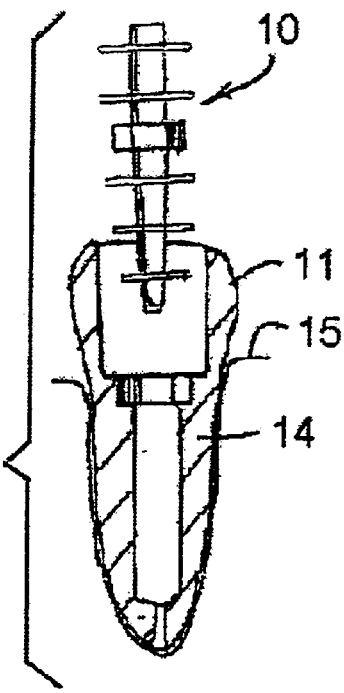
FIG. 4 shows the next step according to the invention, in a view that is similar to FIG. 3, during which a dental post constructed according to the present invention is inserted into the canal.

Next, and as shown in FIG. 3, a non-round, e.g. hexagonal, ultrasonic cutting head 20 is inserted into the initially round countersink 18, to form a corresponding, non-round countersink 21 at the open end of root canal 13. A dental post 10 according to the invention is then inserted as shown in FIG. 4.

Figure 9:
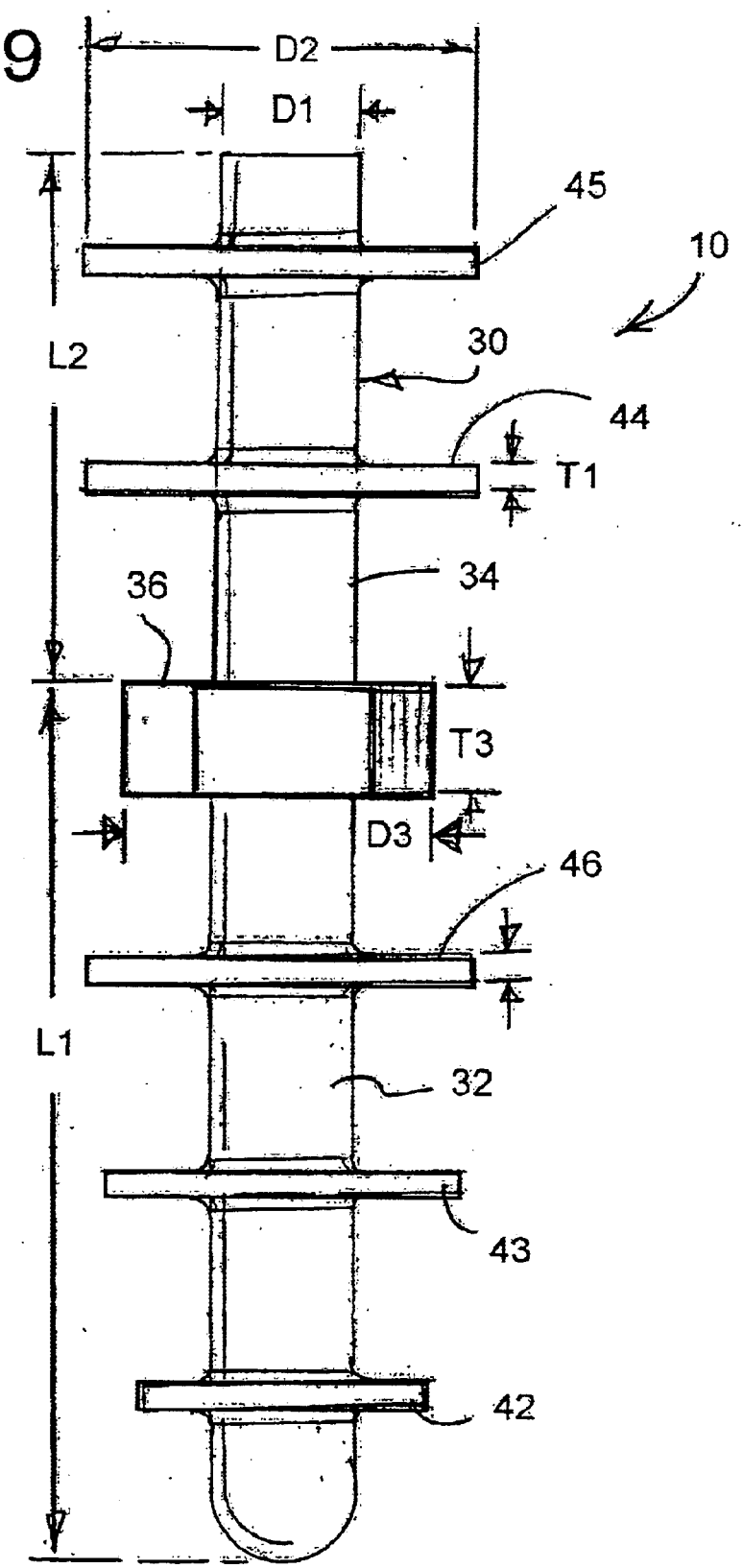
FIG. 9 is a side elevational view of still further embodiment of the post of the present in invention with examples of values for the various dimensions of the post.

As best shown in the enlarged view of FIG. 9, the post 10 has a shank generally designated 30, with a first root engagement portion 32 and a second tooth replacement support portion 34. The post 10 also has a non-round flange 36, formed as one piece with the shank 30 on the first portion 32, but adjacent the second portion 34. In the embodiment shown the non-round flange 36 is hexagonal to match and closely sit in the hexagonal countersink 21. Any non-round shape can be used, however, such as any other type of polygon e.g. having three to twelve or even more sides, or even an oval (FIG. 12) or irregular, non-round shape. The purpose of the flange 36 when it is seated in the corresponding countersink 21, according to the invention, is to prevent the post from rotating in the root canal.

Figure 5:
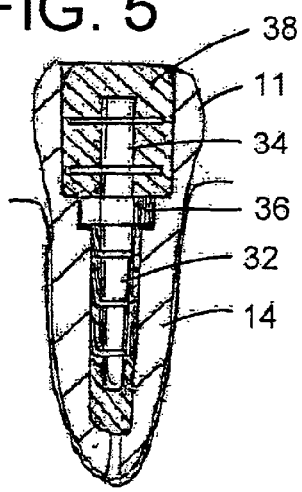
FIG. 5 is a view similar to FIG. 4 of the next step of the invention which uses appropriate cement to fix the post in the root canal and to fill the hollowed out tooth head, serving as a cast, with cement.
Figure 6:
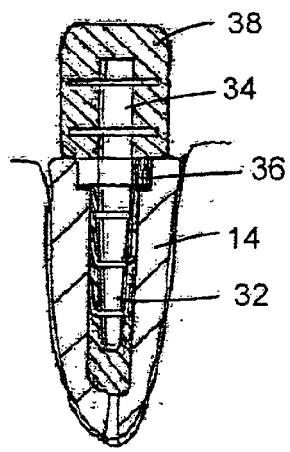
FIG. 6 is a view similar to FIG. 5 of the next step in which the tooth head is removed and the cast and set cement at the top of the post, above the gum line, is shaped to receive a crown or other tooth replacement.

Turning to FIG. 5, the first, root engagement portion 32 is cemented into the hollow canal 13, while the non-round flange 36 is seated into the non-round counter-sink 21 for precluding relative rotation between the post and the root. A luting cement 38 is then filled into the space in natural crown 11, around the second tooth replacement support portion 34, and allowed to cure. The remaining portion of the natural crown 11 acts like a form to cast the cement 38. In FIG. 6, the remaining natural crown 11 is cut away by the dentist and the hardened cement 38 is shaped for receiving an artificial crown 12 (or bridge hardware or any other known tooth replacement structure). In FIG. 7 the crown 12 is cemented with cement 40, to the casing 38 and thus to the second portion 34 of the shank 30.

The dental post of the invention, as shown, for example, in FIGS. 8 and 9, also include at least one flexible flange 42, 43, 44, 45 and/or 46, formed as one piece with the shank 30, and extending outwardly from one of the first and second portions 32, 34 of the shank. The shank, non-round flange and flexible flanges are advantageously make of reinforced of non-reinforced plastic of suitable composition that is cast or injection molded as one piece.

In one preferred embodiment of the invention both the first, root engaging portion 32 and the second, tooth replacement support portion 34 have from one to three flexible flanges. In FIG. 8 both have two and in FIG. 9 the fist portion 32 has three and the second portion 34 has two. FIG. 10 illustrated a further embodiment having a tapered first root engaging portion 32 of the shank with no flange and in FIG. 11, the tapered shank has one flexible flange. FIG. 10 also shows two flexible flanges 47 and 48 on the second shank portion 34 of specialized shape for treating pre-molars and molars. In this case, the flanges 47, 48 cantilever or overhang to one side of the shank 30, over additional areas of the tooth. Optional holes 50 and 51 can be provided in flanges 47 and 48, to receive a short rod that would be cast with the flanges in the cement to better stabilize the support structure to the crown.

In FIG. 11 the cantilevered flanges 52 and 53 are approximately triangular to extend over an appropriate area of the tooth root. See also FIG. 12 where a post similar to that of FIG. 11 is installed to support a crown 12. To increase retention, perforations 56 are provided in the larger flanges such as flanges 52 and 53, for the cement to enter and integrate more fully with the support structure and crown.

Any known, biocompatible, strong yet flexible plastic or polymer, that is also compatible with the types of cements that would be needed to secure the post to the root and to secure the crown or other tooth replacement to the post, can be used to make the dental post of the present invention.

Examples include: polyamide (PA or Nylon), a thermoplastic polycondensate used to make parts of moderate strength; melamine formaldehyde (MF), thermoset polycondensate used in molding items with high surface hardness and scratch resistance; polyvinylchloride (PVC), thermoplastic polymer used for medical applications in rigid grades; polyethylene (PE), thermoplastic polymer with good toughness polyurethane (PU), thermoplastic or thermoset with high impact resistance and chemical and abrasion resistance; polyester, thermoplastic or thermoset polycondensate with excellent dimensional stability and good toughness; polypropylene (PP), a thermoplastic polymer used to make medical syringes with high resistance to flexing but excellent for living hinges, good strength and chemical resistance, good impact strength, and high solvent resistance; polyimide (PI), thermoplastic or thermoset polycondensate with high impact heat resistance and low coefficient of thermal expansion; polyacetal (acetal), thermoplastic used in quality handles, knobs, and bearing parts with good dimensional stability, resistance to creep and atigue, high abrasion and chemical resistance; polycarbonate (PC), thermoplastic polycondensate used to make optical lenses and medical items with excellent strength and toughness, good dimensional stability and impact resistance; acrylonitrile-butadiene-Styrene (ABS), thermoplastic used in consumer products and being tough, hard and rigid with good chemical resistance and dimensional stability; polyetheretherketone (PEEK), thermoplastic polycondensate with high tensile and flexural strength, high impact strength, and a high fatigue limit; or ionomer, a thermoplastic polymer with tough and scratch-resistant qualities.

The skilled artisan can select other plastic materials as well.

As mentioned, the first portion 32 is either cylindrical or tapered, and the second portion 34 is cylindrical. The ends of the shank may be rounded or flat and outer surfaces of all or parts of the post are textured, roughened or provided with regular grooves and/or ridges (knurling) to help positively connect the post to the cement.

The flexible flange or flanges on the root portion 32 are designed to flex upwardly (see FIG. 5 for radially longer flanges and FIG. 12 for radially shorter flanges) to wedge against the inner surface of root canal 13 and help better fix the post in place. The flange of flanges on the tooth replacement support portion 34 help better fix the post to the cast cement 38, and ultimately to the crown 12.

Referring to FIG. 9 and the following table, a typical value, a preferred range and an extreme range of dimensions for the various parts of the post 10 are listed. The shank diameter is D1, the flange diameter (or maximum dimension in the case of non-round flanges) is D2, the non-round flange 36 maximum dimension is D3, the flange thickness is T1 for the shank portion 34, T2 for the shank portion 32, and T3 for flange 36, the first root engaging portion 32 has a length L1 and the second portion 34 has a length L2.

The different dimensions are for different sizes and types of teeth and for different extents of gripping action for the flanges. All dimensions are in millimeters (mm)

TABLE

| Dimension | Typical | Preferred Range | Extreme Range |
|-----------|---------|-----------------|---------------|
| D1 | 1.0 | 0.9 to 1.25 | 0.6 to 2.0 |
| D2 | 4.0 | 3.0 to 5.0 | 2.4 to 8.0 |
| D3 | 7.0 | 5.0 to 9.0 | 3.0 to 11.0 |
| T1 | 1.5 | 0.5 to 1.8 | 0.20 to 2.0 |
| T2 | 1.5 | 0.5 to 1.8 | 0.20 to 2.0 |
| T3 | 3.0 | 2.0 to 4.0 | 1.0 to 5.0 |
| L1 | 6.0 | 4.0 to 7.0 | 3.0 to 9.0 |
| L2 | 10.5 | 8.0 to 13.0 | 5.0 to 15.0 |

While specific embodiments of the invention have been shown and described in detail to illustrate the application of the principles of the invention, it will be understood that the invention may be embodied otherwise without departing from such principles.

What is claimed is:

1. A dental post for supporting a tooth replacement on a natural tooth root, the tooth root having a hollow canal from which a nerve has been removed, the canal having an outer opening, and the root having a non-round countersink at the top of the tooth root, communicating with the canal opening, the post comprising:

a shank having a first root engagement portion for extending into the hollow canal, and a second tooth replacement support portion for extending out of the canal; a non-round flange formed as one piece with the shank on the first portion but adjacent the second portion, the non-round flange being adapted to be received in the non-round countersink for precluding relative rotation between the post and the root when the first root engagement portion is in the root; and at least one flexible flange formed as one piece with the shank and extending outwardly from one of the first and second portions of the shank.

2. A dental post according to claim 1, wherein the at least one flexible flange extends outwardly from the first root engagement portion.

3. A dental post according to claim 1, wherein the at least one flexible flange extends outwardly from the second tooth replacement portion.

4. A dental post according to claim 1, wherein the shank with non-round flange and flexible flange is made of one piece of plastic.

5. A dental post according to claim 1, wherein the non-round flange is polygonal.

6. A dental post according to claim 1, wherein the non-round flange is ovoid.

7. A dental post according to claim 1, the flexible flange being perforated and cantilevered with respect to the shank.

8. A dental post for supporting a tooth replacement on a natural tooth root, the tooth root having a hollow canal from which a nerve has been removed, the canal having an outer opening, and the root having a non-round countersink at the top of the tooth root, communicating with the canal opening, the post comprising:

a shank having a first root engagement portion for extending into the hollow canal, and a second tooth replacement support portion for extending out of the canal; a non-round flange formed as one piece with the shank on the first portion but adjacent the second portion, the non-round flange being adapted to be received in the non-round countersink for precluding relative rotation between the post and the root when the first root engagement portion is in the root; and wherein the shank with non-round flange is made of one piece of plastic.

9. A dental post according to claim 8, wherein the non-round flange is polygonal.

10. A dental post according to claim 8, wherein the non-round flange is ovoid.

11. A method of mounting a tooth replacement to a natural tooth root, comprising:

drilling a hollow canal in the tooth root, the canal having an outer opening;

drilling a round countersink at the top of the tooth root, communicating with the canal opening;

ultrasonically cutting the round countersink to form a non-round countersink;

providing a dental post having a shank with a first root engagement portion and a second tooth replacement support portion, the post also having a non-round flange formed as one piece with the shank on the first portion but adjacent the second portion;

cementing the first portion of the shank into the hollow canal while seating the non-round flange into the non-round countersink for precluding relative rotation between the post and the root; and cementing a tooth replacement to the second portion of the shank.

12. A method according to claim 11, including providing at least one flexible flange as one piece with the shank, extending outwardly from one of the first and second portions of the shank.

13. A method according to claim 12, wherein the at least one flexible flange extends outwardly from the first root engagement portion.

14. A method according to claim 12, wherein the at least one flexible flange extends outwardly from the second tooth replacement portion.

15. A method according to claim 12, wherein the shank with non-round and flexible flange is made of one piece of plastic.

16. A method according to claim 11, wherein the shank with non-round flange is made of one piece of plastic.

17. A method according to claim 11, wherein the first portion is one of cylindrical and tapered, and the second portion is cylindrical.

18. A method according to claim 11, wherein the non-round flange is polygonal.

19. A method according to claim 11, wherein the non-round flange is ovoid.

20. A method according to claim 11, including providing at least one flexible flange as one piece with the shank, extending outwardly from the first portion of the shank, the flexible flange being perforated and cantilevered with respect to the shank.

21. A dental post for supporting a tooth replacement on a natural tooth root, the tooth root having a hollow canal from which a nerve has been removed, the canal having an outer opening, and the root having a non-round countersink at the top of the tooth root, communicating with the canal opening, the post comprising:

a shank having a first root engagement portion for extending into the hollow canal, and a second tooth replacement support portion for extending out of the canal; a non-round flange formed as one piece with the shank on the first portion but adjacent the second portion, the non-round flange being adapted to be received in the non-round countersink for precluding relative rotation between the post and the root when the first root engagement portion is in the root; and wherein the first portion is one of cylindrical and tapered, and the second portion is cylindrical.

22. A dental post according to claim 21, wherein the non-round flange is polygonal.

23. A dental post according to claim 21, wherein the non-round flange is ovoid.

* * * * *